United States Patent [19]

Ohta et al.

[11] Patent Number: 5,753,507
[45] Date of Patent: May 19, 1998

[54] PLANT GERANIOL/NEROL 10-HYDROXYLASE AND DNA CODING THEREFOR

[75] Inventors: Daisaku Ohta, Cary, N.C.; Masaharu Mizutani, Nishikyo-ku, Japan

[73] Assignee: Novartis Finance Corporation, New York, N.Y.

[21] Appl. No.: 532,065

[22] Filed: Sep. 22, 1995

[51] Int. Cl.$^6$ .............................. C12N 5/00; C12N 15/00; C07H 21/04

[52] U.S. Cl. .................. 435/419; 435/172.3; 435/252.3; 435/254.2; 435/320.1; 435/348; 536/23.2; 536/23.6; 935/9; 935/67; 935/69; 935/70

[58] Field of Search .......................... 536/236; 800/205; 435/172.3, 69.1, 320.1, 419, 348, 325, 252.1, 255.1, 252.3, 254.2; 47/58; 935/9, 22, 67, 69, 70, 72, 60, 64

[56] References Cited

U.S. PATENT DOCUMENTS

| | | | |
|---|---|---|---|
| 4,749,787 | 6/1988 | Guanasekera | 540/478 |
| 4,831,133 | 5/1989 | Goodbody et al. | 540/478 |
| 4,910,138 | 3/1990 | Miura et al. | 435/119 |

FOREIGN PATENT DOCUMENTS

WO 93/20206  10/1993  WIPO.

OTHER PUBLICATIONS

Mangold et al., "Gene and cDNA for play cytochrome P450 proteins (CYP72 family) from *Catharanthus roseus*, and transgenic expression of the gene and a cDNA in tobacco and *Arabidopsis thaliana*", *Plant Science*, 96: 129–136 (1994).

Meijer et al., "Isolation of cytochrome P450 cDNA clones from the higher plant *Catharanthus roseus* by a PCR strategy", *Plant Molecular Biology*, 222: 379–383 (1993).

Newman et al., "Arabidopsis thaliana cDNA clone B72TP", *EMBL Database* entry AT016, Accession No. T04016, (1993).

Balsevich et al., "Efficient Incorporation of 10-Hydroxygeraniol and 10-Hydroxynerol into Indole Alkaloids by a Cell Suspension Culture of *Catharanthus roseus*", *Planta Med.* 44(4): 231–233 (1982).

Battersby, et al., "Biosynthesis of Loganin and the Indole Alkaloids from Hydroxygeraniol–Hydroxynerol" *J. Chem. Soc. D. Chem. Comm.* 13: 827–828 (1970).

Beltzer et al., "Charged Residues Are Major Determinants of the Transmembrane Orientation of a Signal–Anchor Sequence", *J. Biol. Chem.* 266: 973–978 (1991).

Charlwood et al., "Terpenoid production in plant cell cultures" *Ecological Chemistry and Biochemistry of Plant Terpenoids*, pp. 95–132, [J.B. Harbone, ed.] Clarendon Press (1991).

DeLuca et al., "The Biosynthesis of Monoterpenoid Indole Alkaloids in *Catharanthus roseus*", *Biosynthesis and Molecular Regulation of Amnio Acids in Plants*, pp. 275–284 [B.K. Singh, ed.] (1992).

Edwards et al., "Orientation of Cytochromes P450 in the Endoplasmic Reticulum", *Biochemistry* 30: 71–76 (1991).

Escher, et al., "The Role of Hydroxygeraniol and Hydroxynerol in the Biosynthesis of Loganin and Indole Alkaloids", *J. Chem. Soc. D. Chem. Comm.* 13: 823–825 (1970).

Hallahan et al., "Potential of Secondary Metabolites in Genetic Engineering of Crops for Resistance", *Plant Genetic Manipulation for Crop Protection*, pp. 215–248 [Gatehouse, A.M.R., ed.] CAB International (1992).

Hallahan et al., "Plant cytochrome P–450 and agricultural biotechnology", *Biochemical Society Transactions* 21: 1068–1073 (1993).

Kurz et al. "Biosynthesis and Accumulation of Indole Alkaloids in Cell Suspension Cultures of *Catharanthus roseus* Cultivars", *Primary and Secondary Metabolism in Plant Cell Cultures*, pp. 143–153 [Neumann et al. ed.], Springer-Verlag (1985).

Madyastha et al, "Subcellular Localization of a Cytochrome P–450 Dependent Monooxygenase in Vesicles of the Higher Plant *Catharanthus roseus*", *J. Cell Biology* 72: 302–313 (1977).

Madyastha et al. "Characterization of a Cytochrome P–450 Dependent Monoterpene Hydroxylase from the Higher Plant *Vinca rosea*", *Biochem.* 15:1097–1102 (1976).

Madyastha et al., "Enzymology of Indole Alkaloid Biosynthesis", *Recent Advances in Phytochemistry*, 13: 85–129 91978).

McFarlane et al., "Regulation of Secondary Metabolism in Higher Plants", *Biochem Biophys. Res. Comm.* 66: 1263–1269 (1975).

Meijer et al., "Purification of the cytochrome P–450 enzyme geraniol 10–hydroxylase from cell cultures of *Catharanthus roseus*", *J. Chromatography* 635: 237–249 (1993).

(List continued on next page.)

*Primary Examiner*—Bruce R. Campell
*Attorney, Agent, or Firm*—J. Timothy Meigs

[57] ABSTRACT

The present invention provides novel plant DNA sequences coding for geraniol/nerol 10-hydroxylase (G10H). Methods for using the complete or partial G10H coding sequence as a probe for diagnostic, mapping and other purposes are taught. Generation of transformed host cells capable of expressing G10H is also taught. Also included is a method for enhancing levels of terpenoid indole alkaloid and/or iridoid insect pheromone produced by a plant. Resulting transgenic plant tissues, including whole plants, having enhanced levels of terpenoid indole alkaloids and/or iridoid insect pheromones are also provided.

17 Claims, No Drawings

OTHER PUBLICATIONS

Mizutani et al., "Purification and Characterization of a Cytochrome P450 (trans-Cinnamic Acid 4-Hydroxylase) from Etiolated Mung Bean Seedlings", *Plant Cell Physiol.* 34: 481–488 (1987).

Schiel et al., "Geraniol-10-hydroxylase Activity and Its Relation to Monoterpene Indoles Alkaloid Acumulation in Cell Suspension Cultures of *Catharanthus roseus*", *Z. Naturforsch,* 42c: 1075–1081 (1987).

Schiel et al., "Geraniol-10-hydroxylase of *Catharanthus roseus* and its Correlation with Indole Alkaloid Biosynthesis", *Planta Med.,* (5): 422, K14 (1986).

Van der Heijden et al., "High-Performance Liquid Chromatographic Determination of Indole Alkaloids in a Suspension Culture of *Tabernaemontana Divaricata*" *J Chromatogr* 396:287–295 (1987).

Van der Heijden et al., "Pharmacognostical studies of Tabernaemontana species: XX Ion-pair ddroplet counter-current chromatography of indole alkaloids from suspension cultures", *J Chromatogr* 396: 410–415 (1987).

JD Watson et al (1987) Molecular Biology of the Gene, p. 313.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1893 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Arabidopsis thaliana ( v i i ) IMMEDIATE SOURCE:
        ( B ) CLONE: P450-4

( i x ) FEATURE:
        ( A ) NAME/KEY: CDS
        ( B ) LOCATION: 6..1490

( x i ) SEQUENCE DESCRIPTION: SEQ ID NO:1:

```
CACAG ATG GAC ATA ATC TCA GGG CAA GCT CTG TTA CTC CTC TTT TGC             47
      Met Asp Ile Ile Ser Gly Gln Ala Leu Leu Leu Leu Phe Cys
       1               5                  10

TTT ATC TTA TCA TGT TTT CTT ATC TTC ACC ACC ACA AGA TCT GGA CGA            95
Phe Ile Leu Ser Cys Phe Leu Ile Phe Thr Thr Thr Arg Ser Gly Arg
 15              20                  25                  30

ATC TCC CGC GGG GCC ACC GCG CTG CCT CCA GGA CCT CCA CGG TTA CCG           143
Ile Ser Arg Gly Ala Thr Ala Leu Pro Pro Gly Pro Pro Arg Leu Pro
                 35                  40                  45

ATC ATC GGA AAT ATT CAC CTC GTC GGA AAA CAT CCA CAT CGC TCA TTC           191
Ile Ile Gly Asn Ile His Leu Val Gly Lys His Pro His Arg Ser Phe
             50                  55                  60

GCC GAG CTC TCA AAA ACT TAT GGA CCA GTC ATG AGT CTT AAG CTT GGA           239
Ala Glu Leu Ser Lys Thr Tyr Gly Pro Val Met Ser Leu Lys Leu Gly
         65                  70                  75

AGT TTA AAT ACA GTG GTT ATA GCT TCA CCA GAA GCT GCG AGA GAG GTT           287
Ser Leu Asn Thr Val Val Ile Ala Ser Pro Glu Ala Ala Arg Glu Val
     80                  85                  90

TTA CGA ACA CAT GAC CAG ATT TTG TCT GCC CGT AGT CCC ACT AAC GCG           335
Leu Arg Thr His Asp Gln Ile Leu Ser Ala Arg Ser Pro Thr Asn Ala
 95                 100                 105                 110

GTA CGG TCC ATC AAT CAC CAA GAC GCT TCC CTT GTC TGG CTT CCT TCG           383
Val Arg Ser Ile Asn His Gln Asp Ala Ser Leu Val Trp Leu Pro Ser
                 115                 120                 125

TCG TCC GCT CGT TGG AGG CTG TTG AGA AGG CTG TCG GTG ACT CAG CTC           431
Ser Ser Ala Arg Trp Arg Leu Leu Arg Arg Leu Ser Val Thr Gln Leu
             130                 135                 140

TTG TCA CCA CAG CGT ATC GAA GCC ACG AAA GCC TTG AGG ATG AAC AAG           479
Leu Ser Pro Gln Arg Ile Glu Ala Thr Lys Ala Leu Arg Met Asn Lys
         145                 150                 155

GTG AAG GAA CTT GTG AGC TTC ATA AGT GAA AGC AGC GAT AGG GAA GAA           527
Val Lys Glu Leu Val Ser Phe Ile Ser Glu Ser Ser Asp Arg Glu Glu
     160                 165                 170

TCT GTT GAT ATT TCT CGT GTA GCC TTC ATC ACA ACT CTT AAT ATC ATA           575
Ser Val Asp Ile Ser Arg Val Ala Phe Ile Thr Thr Leu Asn Ile Ile
 175                 180                 185                 190

TCG AAC ATT CTG TTT TCC GTC GAT CTC GGT AGC TAC AAC GCG AAA GCT           623
Ser Asn Ile Leu Phe Ser Val Asp Leu Gly Ser Tyr Asn Ala Lys Ala
                 195                 200                 205

TCT ATT AAT GGG GTT CAA GAC ACG GTG ATT AGT GTT ATG GAT GCT GCC           671
Ser Ile Asn Gly Val Gln Asp Thr Val Ile Ser Val Met Asp Ala Ala
             210                 215                 220
```

| | | | | | | | | | | | | | | | | |
|---|---|---|---|---|---|---|---|---|---|---|---|---|---|---|---|---|
| GGG | ACT | CCA | GAC | GCT | GCT | AAT | TAC | TTT | CCA | TTT | CTG | AGG | TTT | CTT | GAT | 719 |
| Gly | Thr | Pro | Asp | Ala | Ala | Asn | Tyr | Phe | Pro | Phe | Leu | Arg | Phe | Leu | Asp | |
| | | 225 | | | | | 230 | | | | | 235 | | | | |
| CTG | CAA | GGT | AAT | GTG | AAG | ACT | TTT | AAG | GTT | TGC | ACG | GAG | AGG | CTG | GTA | 767 |
| Leu | Gln | Gly | Asn | Val | Lys | Thr | Phe | Lys | Val | Cys | Thr | Glu | Arg | Leu | Val | |
| | 240 | | | | | 245 | | | | | 250 | | | | | |
| AGG | GTT | TTC | CGT | GGG | TTC | ATT | GAT | GCT | AAG | ATT | GCG | GAA | AAA | TCA | TCG | 815 |
| Arg | Val | Phe | Arg | Gly | Phe | Ile | Asp | Ala | Lys | Ile | Ala | Glu | Lys | Ser | Ser | |
| 255 | | | | | 260 | | | | | 265 | | | | | 270 | |
| CAG | AAT | AAC | CCT | AAA | GAT | GTT | TCA | AAA | AAC | GAT | TTC | GTT | GAC | AAC | CTT | 863 |
| Gln | Asn | Asn | Pro | Lys | Asp | Val | Ser | Lys | Asn | Asp | Phe | Val | Asp | Asn | Leu | |
| | | | | 275 | | | | | 280 | | | | | 285 | | |
| CTC | GAT | TAC | AAA | GGA | GAT | GAA | TCA | GAA | CTC | TCC | ATT | AGC | GAT | ATT | GAA | 911 |
| Leu | Asp | Tyr | Lys | Gly | Asp | Glu | Ser | Glu | Leu | Ser | Ile | Ser | Asp | Ile | Glu | |
| | | | 290 | | | | | 295 | | | | | 300 | | | |
| CAC | CTT | CTC | TTG | GAT | ATG | TTT | ACA | GCA | GGC | ACG | GAT | ACA | AGC | TCT | AGT | 959 |
| His | Leu | Leu | Leu | Asp | Met | Phe | Thr | Ala | Gly | Thr | Asp | Thr | Ser | Ser | Ser | |
| | | 305 | | | | | 310 | | | | | 315 | | | | |
| ACC | CTG | GAG | TGG | CCA | ATG | ACA | GAG | TTA | CTT | AAA | AAC | CCT | AAA | ACG | ATG | 1007 |
| Thr | Leu | Glu | Trp | Pro | Met | Thr | Glu | Leu | Leu | Lys | Asn | Pro | Lys | Thr | Met | |
| | 320 | | | | | 325 | | | | | 330 | | | | | |
| GCG | AAA | GCT | CAG | GCC | GAG | ATC | GAT | TGT | GTG | ATA | GGT | CAA | AAC | GGT | ATC | 1055 |
| Ala | Lys | Ala | Gln | Ala | Glu | Ile | Asp | Cys | Val | Ile | Gly | Gln | Asn | Gly | Ile | |
| 335 | | | | | 340 | | | | | 345 | | | | | 350 | |
| GTT | GAA | GAG | TCA | GAT | ATC | TCC | AAA | CTG | CCG | TAT | TTA | CAA | GCA | GTC | GTG | 1103 |
| Val | Glu | Glu | Ser | Asp | Ile | Ser | Lys | Leu | Pro | Tyr | Leu | Gln | Ala | Val | Val | |
| | | | | 355 | | | | | 360 | | | | | 365 | | |
| AAG | GAA | ACT | TTC | CGG | TTA | CAT | ACG | CCT | GTT | CCG | CTT | CTT | ATC | CCG | CGA | 1151 |
| Lys | Glu | Thr | Phe | Arg | Leu | His | Thr | Pro | Val | Pro | Leu | Leu | Ile | Pro | Arg | |
| | | | 370 | | | | | 375 | | | | | 380 | | | |
| AAA | GCC | GAA | TCC | GAT | GCG | GAG | ATT | CTT | GGT | TTC | ATG | GTG | CTT | AAA | GAT | 1199 |
| Lys | Ala | Glu | Ser | Asp | Ala | Glu | Ile | Leu | Gly | Phe | Met | Val | Leu | Lys | Asp | |
| | | 385 | | | | | 390 | | | | | 395 | | | | |
| ACT | CAG | GTT | CTA | GTG | AAC | GTC | TGG | GCC | ATA | GGA | CGA | GAC | CCG | AGC | GTG | 1247 |
| Thr | Gln | Val | Leu | Val | Asn | Val | Trp | Ala | Ile | Gly | Arg | Asp | Pro | Ser | Val | |
| | 400 | | | | | 405 | | | | | 410 | | | | | |
| TGG | GAT | AAT | CCG | TCC | CAG | TTT | GAG | CCA | GAG | AGG | TTT | TTG | GGG | AAA | GAT | 1295 |
| Trp | Asp | Asn | Pro | Ser | Gln | Phe | Glu | Pro | Glu | Arg | Phe | Leu | Gly | Lys | Asp | |
| 415 | | | | | 420 | | | | | 425 | | | | | 430 | |
| ATG | GAC | GTG | AGA | GGT | AGA | GAT | TAT | GAG | CTT | ACA | CCA | TTC | GGC | GCC | GGA | 1343 |
| Met | Asp | Val | Arg | Gly | Arg | Asp | Tyr | Glu | Leu | Thr | Pro | Phe | Gly | Ala | Gly | |
| | | | | 435 | | | | | 440 | | | | | 445 | | |
| CGT | AGA | ATT | TGC | CCG | GGA | ATG | CCT | TTG | GCT | ATG | AAA | ACA | GTG | TCT | CTT | 1391 |
| Arg | Arg | Ile | Cys | Pro | Gly | Met | Pro | Leu | Ala | Met | Lys | Thr | Val | Ser | Leu | |
| | | | 450 | | | | | 455 | | | | | 460 | | | |
| ATG | CTT | GCT | TCT | CTT | CTT | TAT | TCC | TTT | GAC | TGG | AAG | CTT | CCG | AAG | GGT | 1439 |
| Met | Leu | Ala | Ser | Leu | Leu | Tyr | Ser | Phe | Asp | Trp | Lys | Leu | Pro | Lys | Gly | |
| | | 465 | | | | | 470 | | | | | 475 | | | | |
| GTC | CTT | TCG | GAG | GGA | TTT | GGA | CAT | GGA | CGA | GAC | CTT | TGG | TCT | AAC | TTT | 1487 |
| Val | Leu | Ser | Glu | Gly | Phe | Gly | His | Gly | Arg | Asp | Leu | Trp | Ser | Asn | Phe | |
| | 480 | | | | | 485 | | | | | 490 | | | | | |
| GCA | TAAGACCCAA | CCCGTTACAT | GCCGTACCCG | TCCAAGAAAC | GCGCCAATAT | | | | | | | | | | | 1540 |
| Ala | | | | | | | | | | | | | | | | |
| 495 | | | | | | | | | | | | | | | | |

```
TAATTAGTCG TGGTTTTATA ATTAAAAATA AACAGAGAAA TAATCTCCAA AGCTTTGTTT        1600
ATTACCCAAA AACTATCTGT TTTCGGTTCT AGAGTTTGTT TGTTTCTCTC TCTTGAGGTG        1660
GCTAGAGCTT GAAGAAGTCA AAAGTATCCA TATTGATGCC TAGCTTCGGT CCTCGGTTTA        1720
GGCTAGGAAG GAAACGAAGA AGTTTCTGCA AACCGATGCA GATCATCAAT GGAATAATGA        1780
```

```
AATGTTAATT  TTATCATTTA  CTCATATAGG  TTTCCGCCTC  ATTATCATTT  ACTTGATGTT      1840

TCTCCTAAAT  CTTGTCATTT  AATTGACTAA  GGAAATAACG  AAGAAATCTC  GTG             1893
```

( 2 ) INFORMATION FOR SEQ ID NO:2:

( i ) SEQUENCE CHARACTERISTICS:
        ( A ) LENGTH: 495 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asp  Ile  Ile  Ser  Gly  Gln  Ala  Leu  Leu  Leu  Leu  Phe  Cys  Phe  Ile
  1              5                        10                       15

Leu  Ser  Cys  Phe  Leu  Ile  Phe  Thr  Thr  Thr  Arg  Ser  Gly  Arg  Ile  Ser
               20                        25                  30

Arg  Gly  Ala  Thr  Ala  Leu  Pro  Pro  Gly  Pro  Pro  Arg  Leu  Pro  Ile  Ile
          35                        40                  45

Gly  Asn  Ile  His  Leu  Val  Gly  Lys  His  Pro  His  Arg  Ser  Phe  Ala  Glu
     50                        55                  60

Leu  Ser  Lys  Thr  Tyr  Gly  Pro  Val  Met  Ser  Leu  Lys  Leu  Gly  Ser  Leu
 65                  70                       75                        80

Asn  Thr  Val  Val  Ile  Ala  Ser  Pro  Glu  Ala  Ala  Arg  Glu  Val  Leu  Arg
                    85                       90                       95

Thr  His  Asp  Gln  Ile  Leu  Ser  Ala  Arg  Ser  Pro  Thr  Asn  Ala  Val  Arg
               100                      105                 110

Ser  Ile  Asn  His  Gln  Asp  Ala  Ser  Leu  Val  Trp  Leu  Pro  Ser  Ser  Ser
          115                      120                 125

Ala  Arg  Trp  Arg  Leu  Leu  Arg  Arg  Leu  Ser  Val  Thr  Gln  Leu  Leu  Ser
     130                      135                 140

Pro  Gln  Arg  Ile  Glu  Ala  Thr  Lys  Ala  Leu  Arg  Met  Asn  Lys  Val  Lys
145                      150                      155                     160

Glu  Leu  Val  Ser  Phe  Ile  Ser  Glu  Ser  Ser  Asp  Arg  Glu  Glu  Ser  Val
                    165                      170                     175

Asp  Ile  Ser  Arg  Val  Ala  Phe  Ile  Thr  Thr  Leu  Asn  Ile  Ile  Ser  Asn
               180                      185                 190

Ile  Leu  Phe  Ser  Val  Asp  Leu  Gly  Ser  Tyr  Asn  Ala  Lys  Ala  Ser  Ile
          195                      200                 205

Asn  Gly  Val  Gln  Asp  Thr  Val  Ile  Ser  Val  Met  Asp  Ala  Ala  Gly  Thr
     210                      215                 220

Pro  Asp  Ala  Ala  Asn  Tyr  Phe  Pro  Phe  Leu  Arg  Phe  Leu  Asp  Leu  Gln
225                      230                      235                     240

Gly  Asn  Val  Lys  Thr  Phe  Lys  Val  Cys  Thr  Glu  Arg  Leu  Val  Arg  Val
                    245                      250                     255

Phe  Arg  Gly  Phe  Ile  Asp  Ala  Lys  Ile  Ala  Glu  Lys  Ser  Ser  Gln  Asn
               260                      265                 270

Asn  Pro  Lys  Asp  Val  Ser  Lys  Asn  Asp  Phe  Val  Asp  Asn  Leu  Leu  Asp
          275                      280                 285

Tyr  Lys  Gly  Asp  Glu  Ser  Glu  Leu  Ser  Ile  Ser  Asp  Ile  Glu  His  Leu
     290                      295                 300

Leu  Leu  Asp  Met  Phe  Thr  Ala  Gly  Thr  Asp  Thr  Ser  Ser  Ser  Thr  Leu
305                      310                      315                     320

Glu  Trp  Pro  Met  Thr  Glu  Leu  Leu  Lys  Asn  Pro  Lys  Thr  Met  Ala  Lys
                    325                      330                     335

Ala  Gln  Ala  Glu  Ile  Asp  Cys  Val  Ile  Gly  Gln  Asn  Gly  Ile  Val  Glu
```

|     |     |     | 340 |     |     |     | 345 |     |     |     | 350 |     |     |
| --- | --- | --- | --- | --- | --- | --- | --- | --- | --- | --- | --- | --- | --- |
| Glu | Ser | Asp | Ile | Ser | Lys | Leu | Pro | Tyr | Leu | Gln | Ala | Val | Lys | Glu |
|     |     | 355 |     |     |     |     | 360 |     |     |     | 365 |     |     |     |
| Thr | Phe | Arg | Leu | His | Thr | Pro | Val | Pro | Leu | Leu | Ile | Pro | Arg | Lys | Ala |
|     | 370 |     |     |     |     | 375 |     |     |     |     | 380 |     |     |     |
| Glu | Ser | Asp | Ala | Glu | Ile | Leu | Gly | Phe | Met | Val | Leu | Lys | Asp | Thr | Gln |
| 385 |     |     |     |     | 390 |     |     |     |     | 395 |     |     |     |     | 400 |
| Val | Leu | Val | Asn | Val | Trp | Ala | Ile | Gly | Arg | Asp | Pro | Ser | Val | Trp | Asp |
|     |     |     |     | 405 |     |     |     |     | 410 |     |     |     |     | 415 |     |
| Asn | Pro | Ser | Gln | Phe | Glu | Pro | Glu | Arg | Phe | Leu | Gly | Lys | Asp | Met | Asp |
|     |     |     | 420 |     |     |     |     | 425 |     |     |     |     | 430 |     |     |
| Val | Arg | Gly | Arg | Asp | Tyr | Glu | Leu | Thr | Pro | Phe | Gly | Ala | Gly | Arg | Arg |
|     |     | 435 |     |     |     |     | 440 |     |     |     |     | 445 |     |     |     |
| Ile | Cys | Pro | Gly | Met | Pro | Leu | Ala | Met | Lys | Thr | Val | Ser | Leu | Met | Leu |
|     | 450 |     |     |     |     | 455 |     |     |     |     | 460 |     |     |     |     |
| Ala | Ser | Leu | Leu | Tyr | Ser | Phe | Asp | Trp | Lys | Leu | Pro | Lys | Gly | Val | Leu |
| 465 |     |     |     |     | 470 |     |     |     |     | 475 |     |     |     |     | 480 |
| Ser | Glu | Gly | Phe | Gly | His | Gly | Arg | Asp | Leu | Trp | Ser | Asn | Phe | Ala |
|     |     |     |     | 485 |     |     |     |     | 490 |     |     |     |     | 495 |

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "sense PCR primer used in
            Example 1"

( i x ) FEATURE:
        ( A ) NAME/KEY: misc_feature
        ( B ) LOCATION: 1..17
        ( D ) OTHER INFORMATION: /note= ""N"nucleotides are inosine
            ("I" in PCR primer sequence set forth in Example 1 of the
        specification)."

( x i ) SEQUENCE DESCRIPTION: SEQ ID NO:3:

AAR Y TNCCNC CNGGNCC                                    17

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Antisense PCR primer used
            in Example 1"

( i x ) FEATURE:
        ( A ) NAME/KEY: misc_feature
        ( B ) LOCATION: 1..25
        ( D ) OTHER INFORMATION: /note= ""N"nucleotides are inosine
            ("I" in PCR primer sequence shown in Example 1 of the
        specification)."

( x i ) SEQUENCE DESCRIPTION: SEQ ID NO:4:

GGRTCNCKNW CNARGCCCAN GCRTT                            25

( 2 ) INFORMATION FOR SEQ ID NO:5:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: Not Relevant ( i i ) MOLECULE TYPE: peptide ( x i ) SEQUENCE DESCRIPTION: SEQ ID NO:5:

Lys  Leu  Pro  Pro  Gly  Pro
1                          5

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:6:

Asn  Ala  Trp  Ala  Leu  Ala  Gly  Arg  Asp  Pro
1                    5                            10

PLANT GERANIOL/NEROL 10-HYDROXYLASE AND DNA CODING THEREFOR

FIELD OF THE INVENTION

The invention relates generally to a plant enzymatic activity involved in the biosynthesis of terpenoid indole alkaloids and iridoid insect pheromones. The invention particularly relates to the plant enzyme geraniol/nerol 10-hydroxylase and the gene coding for this enzyme. The invention further relates to the application of genetic engineering techniques to this enzyme.

BACKGROUND OF THE INVENTION

I. The G10H Enzyme and its Involvement in the Terpenoid Indole Alkaloid Biosynthetic Pathway Terpenoid indole alkaloids represent a class of pharmaceutically useful compounds which naturally occur in many plant species (see, e.g. Hallahan, D. L. et al., *Biochemical Society Transactions*. 21: 1068–1073 (1993); Charlwood, B. V. et al., "Terpenoid production in plant cell cultures in Ecological Chemistry and Biochemistry of Plant Terpenoids", pp 95–132 ed. J. B. Harbone. Clarendon Press (1991); Madyastha, K. M. et al., "Enzymology of Indole Alkaloid Biosynthesis", pp 85–129 of "Recent Advances in Phytochemistry", vol. 13, ed. by Swain, T. and Waller, G. pub. by Plenum Press, NEW YORK (1978); see also Balsevich, J. et al., *Planta Med.* 44(4): 231–233 (1982); Battersby, A. R. et al., *J. Chem. Soc. D. Chem. Comm.* 13: 827–828 (1970); Escher, S. et al., *J. Chem. Soc. D. Chem. Comm.* 13: 823–825 (1970).

One of the enzymes essential to the biosynthesis of terpenoid indole alkaloids in plants is known as geraniol/nerol 10-hydroxylase (referred to herein as "G10H"; see Scheil, O., *Planta Med.* (5): 422 (1986)). The G10H enzyme catalyzes the conversion of geraniol to its 10-hydroxy derivative form, which is the rate-limiting step in the biosynthesis of monoterpenoid indole alkaloids (see Schiel, O. et al., *Z. Naturforsch* 4(9–10)2: 1075 (1987)). Feedback control of this enzyme via inhibition by catharanthine, an end product of the pathway, has been reported (see McFarlane, J. et al., *Biochem Biophys. Res. Comm.* 66: 1263 (1975)). A chart of the monoterpenoid indole alkaloids biosynthetic pathway is provided below.

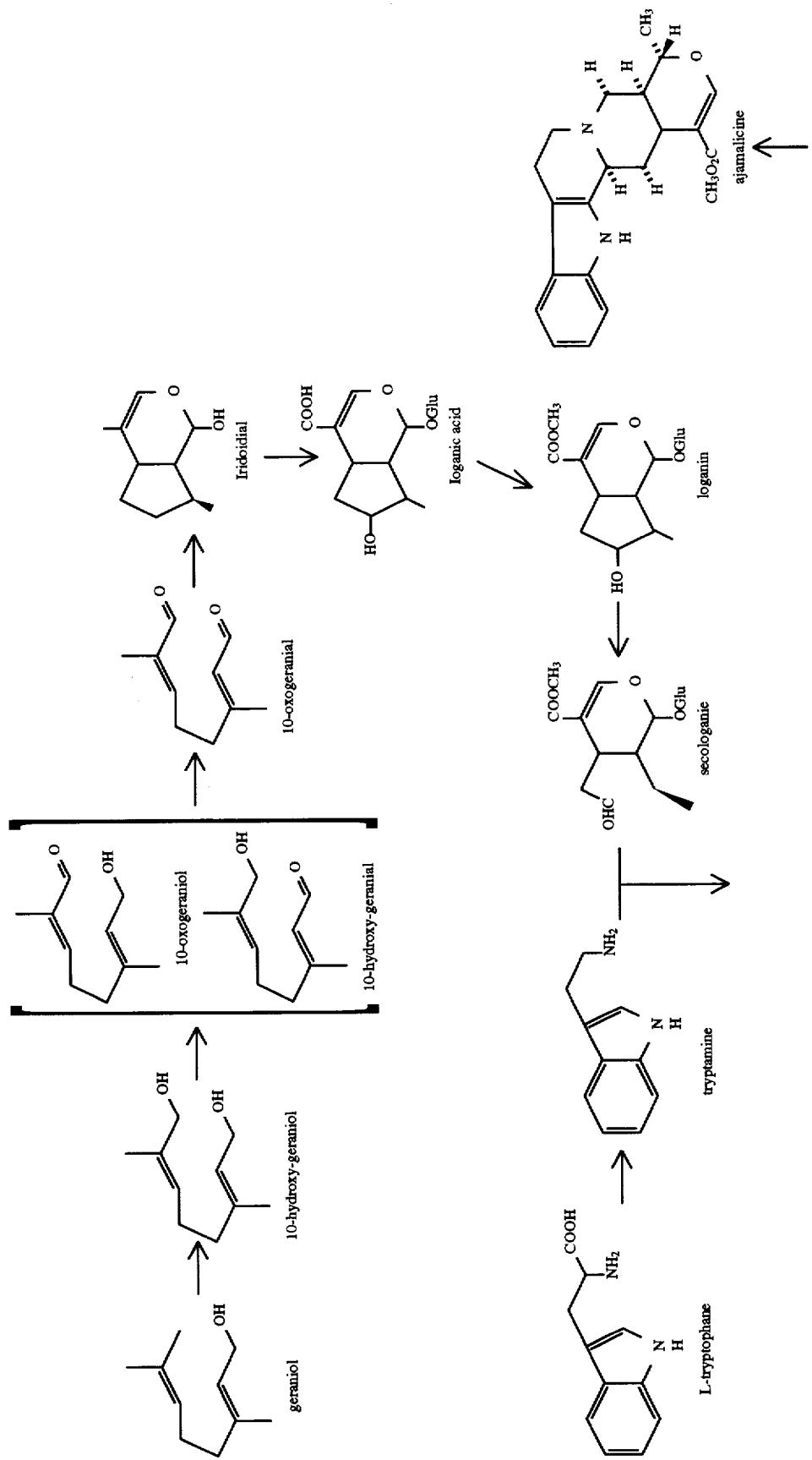

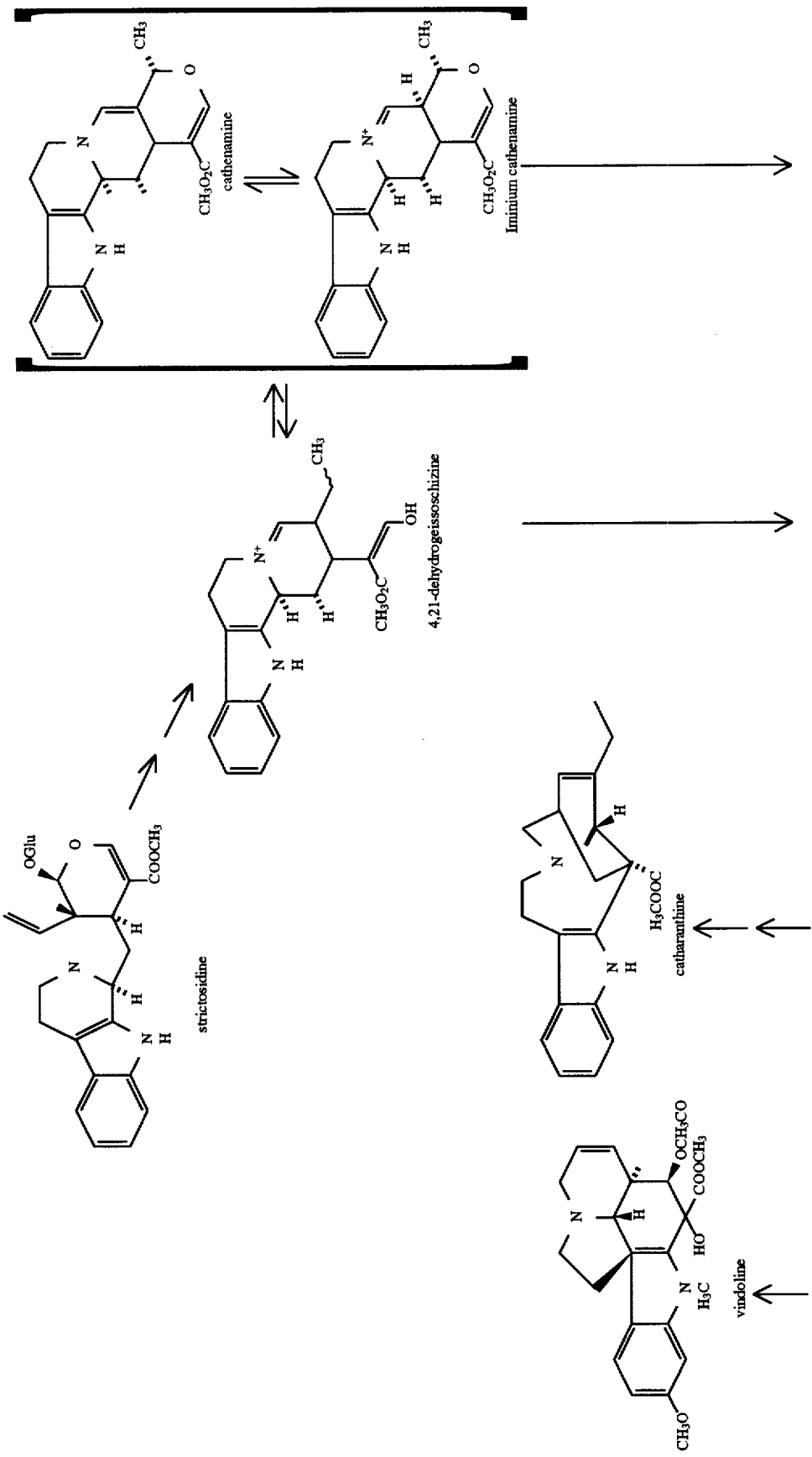

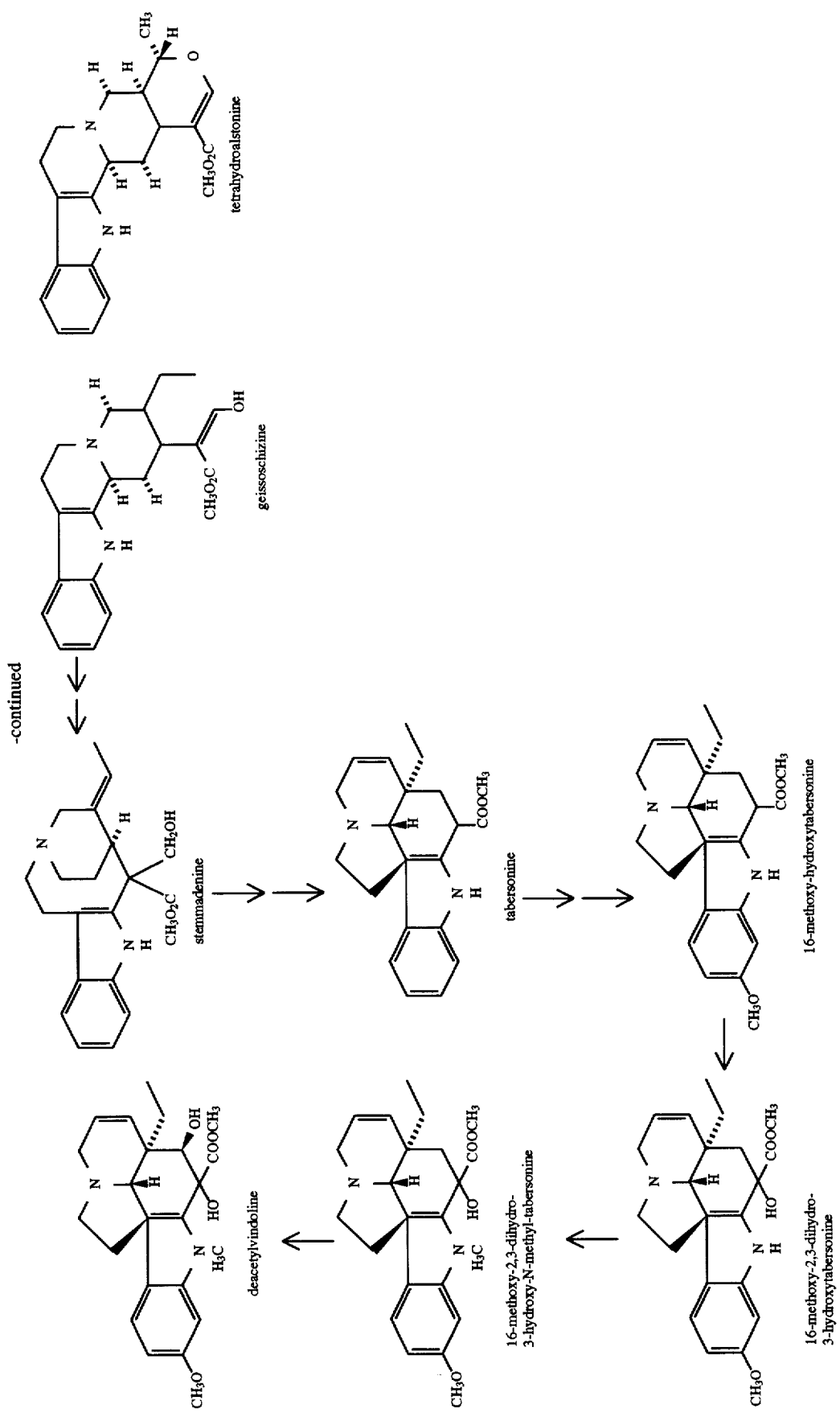
Biosynthetic pathway for the major indole alkaloids of Catharanthus roseus
De Luca et al., The biosynthesis of Monoterpenoid Indole Alkaloids in Catharanthus in "Biosynthesis and Molecular Regulation of Amino Acids in Plants" ed by BK Singh, HE Flores, JC Schannon, pp. 275-284, American Society of Plant Physiologists (1992)

Isolation and purification of the G10H enzyme from *Catharanthus roseus* has been reported (see Meijer, A. H. et al., *J. Chromatography* 635: 237–249 (1993); U.S. Pat. No. 4,831,133 issued May 16, 1989 to Goodbody, A. E. et al.; Madyastha, K. M. et al., *Biochem.* 15: 1097 (1976)). However, genes encoding the G10H enzyme have heretofore not been isolated or characterized from any plant species.

SUMMARY OF THE INVENTION

The present invention provides an isolated DNA molecule encoding the geraniol/nerol 10-hydroxylase (G10H) enzyme from a plant source.

A DNA coding sequence for the G10H enzyme in *Arabidopsis thaliana* is provided in SEQ ID No. 1. Using the information provided by the present invention, the DNA coding sequence for G10H enzyme(s) from any plant source may be obtained using standard methods.

The present invention also embodies the recombinant production of the G10H enzyme, and methods for using recombinantly produced G10H. In particular, methods are provided for enhancing terpenoid indole alkaloid levels, as well as certain iridoid insect pheromones, in a plant by introducing a chimeric gene into the plant which can express the G10H enzyme.

In another aspect of the invention, transgenic plant tissue, including plants, seeds, and cultured tissue, with enhanced levels of terpenoid indole alkaloids and iridoid insect pheromones are provided which comprise one or more chimeric genes expressing a G10H enzyme. This plant tissue may be used as an improved source of pharmaceutically useful terpenoid indole alkaloids such as vinblastine and vincristine. This plant tissue may also be used as an improved source of iridoid insect pheromones which are useful as insect attractants.

DETAILED DESCRIPTION OF THE INVENTION

In one aspect, the present invention is directed to an isolated DNA molecule which encodes a plant geraniol/nerol 10-hydroxylase (referred to herein as "G10H"), the enzyme which catalyzes a rate limiting step in the biosynthesis of terpenoid indole alkaloids. The DNA coding sequence and corresponding amino acid sequence for one G10H enzyme from *Arabidopsis thaliana* are provided as SEQ ID NOS:1 and 2, respectively.

The DNA encoding the G10H enzyme may be isolated from the genome of any plant species which produces terpenoid indole alkaloids according to the invention. Plant G10H coding sequences may be isolated according to well known techniques based on their structural sequence homology to the *Arabidopsis thaliana* G10H coding sequence set forth in SEQ ID No. 1. In these techniques all or part of the known G10H coding sequence is used as a probe which selectively hybridizes to other G10H coding sequences present in the population of cloned genomic DNA fragments or cDNA fragments (i.e. genomic or cDNA libraries) from a chosen organism. Such techniques include hybridization screening of plated DNA libraries (either plaques or colonies; see, e.g., Sambrook et al., *Molecular Cloning*, eds., Cold Spring Harbor Laboratory Press, (1989)) and amplification by PCR using oligonucleotide primers corresponding to sequence domains conserved among known G10H amino acid sequences (see, e.g. Innis et al., *PCR Protocols, a Guide to Methods and Applications* eds., Academic Press (1990)). These methods are particularly well suited to the isolation of G10H coding sequences from organisms closely related to the organism from which the probe sequence is derived. Thus, application of these methods using the Arabidopsis coding sequence as a probe would be expected to be particularly well suited for the isolation of G10H coding sequences from other plant species including monocotyledenous and dicotyledenous species, and more particularly those species most closely related to *Arabidopsis thaliana* within the Cruciferae family.

The isolated plant G10H sequences taught by the present invention may be manipulated according to standard genetic engineering techniques to suit any desired purpose. For example, the entire G10H sequence or portions thereof may be used as probes capable of specifically hybridizing to G10H coding sequences and messenger RNAs. To achieve specific hybridization under a variety of conditions, such probes include sequences that are unique among G10H coding sequences and are preferably at least 20 nucleotides in length, and most preferably at least 50 nucleotides in length. Such probes may be used to amplify and analyze G10H coding sequences from a chosen organism via the well known process of polymerase chain reaction (PCR). This technique may be used to isolate additional G10H coding sequences from a desired organism or as a diagnostic assay to determine the presence of G10H coding sequences in an organism.

G10H specific hybridization probes may also be used to map the location of the native G10H gene(s) in the genome of a chosen plant using standard techniques based on the selective hybridization of the probe to genomic G10H sequences. These techniques include, but are not limited to, identification of DNA polymorphisms identified or contained within the G10H probe sequence, and use of such polymorphisms to follow segregation of the G10H gene relative to other markers of known map position in a mapping population derived from self fertilization of a hybrid of two polymorphic parental lines (see e.g. Helentjaris et al., *Plant Mol. Biol.* 5: 109 (1985). Sommer et al. *Biotechniques* 12:82 (1992); D'Ovidio et al., *Plant Mol. Biol.* 15: 169 (1990)). While any plant G10H sequence is contemplated to be useful as a probe for mapping G10H genes, preferred probes are those G10H sequences from plants more closely related to the chosen plant, and most preferred probes are those G10H sequences from the chosen plant. Mapping of G10H genes in this manner is contemplated to be particularly useful for breeding purposes. For instance, by knowing the genetic map position of a mutant G10H gene that confers increased production of terpenoid indole alkaloids, flanking DNA markers can be identified from a reference genetic map (see, e.g., Helentjaris, *Trends Genet.* 3: 217 (1987)). During introgression of this trait into a new breeding line, these markers can then be used to monitor the extent of G10H-linked flanking chromosomal DNA still present in the recurrent parent after each round of back-crossing.

G10H specific hybridization probes may also be used to quantitate levels of G10H mRNA in a plant using standard techniques such as Northern blot analysis. This technique may be used as a diagnostic assay to detect altered levels of G10H expression.

For recombinant production of the enzyme in a host organism, the plant G10H coding sequence may be inserted into an expression cassette designed for the chosen host and introduced into the host where it is recombinantly produced. The choice of specific regulatory sequences such as promoter, signal sequence, 5' and 3' untranslated sequences, and enhancer appropriate for the chosen host is within the level of skill of the routineer in the art. The resultant molecule, containing the individual elements linked in proper reading frame, may be inserted into a vector capable of being transformed into the host cell. Suitable expression vectors and methods for recombinant production of proteins are well known for host organisms such as *E. coli* (see, e.g. Studier and Moffatt, *J. Mol. Biol.* 189: 113 (1986); Brosius, *DNA* 8: 759 (1989)), yeast (see, e.g., Schneider and Guarente, *Meth. Enzymol.* 194: 373 (1991)) and insect cells (see, e.g., Luckow and Summers, *Bio/Technol.* 6: 47 (1988)). Specific examples include plasmids such as pBluescript (Stratagene, La Jolla, Calif.), pFLAG (International Biotechnologies, Inc., New Haven, Conn.), pTrcHis (Invitrogen, La Jolla, Calif.), and baculovirus expression vectors, e.g., those derived from the genome of *Autographica californica* nuclear polyhedrosis virus (AcMNPV). A preferred baculovirus/insect system is pVL1392/Sf21 cells (Invitrogen, La Jolla, Calif.).

Recombinantly produced plant G10H enzyme can be isolated and purified using a variety of standard techniques. The actual techniques which may be used will vary depending upon the host organism used, whether the G10H enzyme is designed for secretion, and other such factors familiar to the skilled artisan (see, e.g. chapter 16 of Ausubel, F. et al., "Current Protocols in Molecular Biology", pub. by John Wiley & Sons, Inc. (1994).

In one aspect of the invention, the amount of G10H enzyme present in a plant or plant cell is increased by introducing into the plant or plant cell a chimeric gene capable of expressing G10H enzyme in a plant cell. Such a chimeric gene will comprise a promoter capable of regulating gene expression in a plant, operably linked to a DNA sequence which encodes a G10H enzyme, followed by a transcriptional terminator and polyadenylation signal.

Coding sequences for G10H enzymes may be genetically engineered for optimal expression in a particular crop plant. Methods for modifying coding sequences to achieve optimal expression in a particular crop species are well known (see, e.g. Perlak et al., *Proc. Natl. Acad. Sci. USA* 88: 3324 (1991); Koziel et al., *Bio/technol.* 11: 194 (1993)).

A DNA sequence coding for a G10H enzyme may be inserted into an expression cassette designed for plants to construct a chimeric gene according to the invention using standard genetic engineering techniques. The choice of specific regulatory sequences such as promoter, signal sequence, 5' and 3' untranslated sequences, and enhancer appropriate for achieving the desired pattern and level of expression in the chosen plant host is within the level of skill of the routineer in the art. The resultant molecule, containing the individual elements linked in proper reading frame, may be inserted into a vector capable of being transformed into a host plant cell.

Examples of promoters capable of functioning in plants or plant cells (i.e., those capable of driving expression of associated coding sequences such as those coding for G10H enzymes in plant cells) include the cauliflower mosaic virus (CaMV) 19S or 35S promoters and CaMV double promoters; nopaline synthase promoters; pathogenesis-related (PR) protein promoters; small subunit of ribulose bisphosphate carboxylase (ssuRUBISCO) promoters, and the like. Preferred are the rice actin promoter (McElroy et al., *Mol. Gen. Genet.* 231: 150 (1991)), maize ubiquitin promoter (EP 0 342 926; Taylor et al., *Plant Cell Rep.* 12: 491 (1993)), and the PR-1 promoter from tobacco, Arabidopsis, or maize (see U.S. Pat. No. 5,614,395 to Ryals et al., incorporated by reference herein in its entirety). Also preferred are the 35S promoter and an enhanced or double 35S promoter such as that described in Kay et al., *Science* 236: 1299–1302 (1987). The promoters themselves may be modified to manipulate promoter strength to increase expression of the associated coding sequence in accordance with art-recognized procedures. Preferred promoters for use with the present invention will be those which confer high level constitutive expression.

Signal or transit peptides may be fused to the G10H coding sequence in the chimeric DNA constructs of the invention to direct transport of the expressed G10H to the desired site of action. Preferably, G10H should be located in the compartments containing NADPH Cyt-P450 reductase or other oxidoreductases which can donate electrons to P450s such as the endoplasmic reticulum and provacuoles (see Madyastha, K. M. et al. *J. Cell Biology* 72: 302–313 (1977) and chloroplasts (O'Keefe, D. P. et al., *Plant Physiol* 105: 473–482 (1994) or mitochondria (Morohashi, K. et al. *J Biochemistry* 102: 559–568 (1987)). Examples of signal peptides include those natively linked to the plant pathogenesis-related proteins, e.g. PR-1, PR-2, and the like. See, e.g., Payne et al., *Plant Mol. Biol.* 11:89–94 (1988). Examples of transit peptides include the chloroplast transit peptides such as those described in Von Heijne et al., *Plant Mol. Biol. Rep.* 9:104–126 (1991); Mazur et al., *Plant Physiol.* 85: 1110 (1987); Vorst et al., *Gene* 65: 59 (1988), and mitochondrial transit peptides such as those described in Boutry et al., *Nature* 328:340–342 (1987). Also included are sequences that result in localization of the encoded protein to various cellular compartments such as the vacuole. See, for example, Neuhaus et al., *Proc. Natl Acad. Sci. USA* 88: 10362–10366 (1991) and Chrispeels, *Ann. Rev. Plant Physiol. Plant Mol. Biol.* 42: 21–53 (1991). The relevant disclosures of these publications are incorporated herein by reference in their entirety.

The chimeric DNA construct(s) of the invention may contain multiple copies of a promoter or multiple copies of the coding sequence for a G10H enzyme. In addition, the construct(s) may include coding sequences for markers and coding sequences for other peptides such as signal or transit peptides, each in proper reading frame with the other functional elements in the DNA molecule. The preparation of such constructs are within the ordinary level of skill in the art.

Useful markers include peptides providing herbicide, antibiotic or drug resistance, such as, for example, resistance to hygromycin, kanamycin, G418, gentamycin, lincomycin, methotrexate, glyphosate, phosphinothricin, or the like. These markers can be used to select cells transformed with the chimeric DNA constructs of the invention from untransformed cells. Other useful markers are peptidic enzymes which can be easily detected by a visible reaction, for example a color reaction, for example luciferase, β-glucuronidase, or β-galactosidase.

Chimeric genes designed for plant expression such as those described herein can be introduced into the plant cell in a number of art-recognized ways. Those skilled in the art will appreciate that the choice of method might depend on the type of plant (i.e. monocot or dicot) and/or organelle (i.e. nucleus, chloroplast, mitochondria) targeted for transformation. Suitable methods of transforming plant cells include microinjection (Crossway et al., *BioTechniques* 4:320–334 (1986)), electroporation (Riggs et al, *Proc. Natl Acad. Sci. USA* 83:5602–5606 (1986), Agrobacterium mediated transformation (Hinchee et al., *Biotechnology* 6:915–921 (1988) ), direct gene transfer (Paszkowski et al., *EMBO J.* 3:2717–2722 (1984)), and ballistic particle acceleration using devices available from Agracetus, Inc., Madison, Wis.

and Dupont, Inc., Wilmington, Del. (see, for example, Sanford et al., U.S. Pat. No. 4,945,050; and McCabe et al., *Biotechnology* 6:923–926 (1988)).see also, Weissinger et al., *Annual Rev. Genet.* 22:421–477 (1988); Sanford et al., *Particulate Science and Technology* 5:27–37 (1987)(onion); Christou et al., *Plant Physiol.* 87:671–674 (1988)(soybean); McCabe et al., *Bio/Technology* 6:923–926 (1988)(soybean); Datta et al., *Bio/Technology* 8:736–740 (1990)(rice); Klein et al., *Proc. Natl Acad. Sci. USA*, 85:4305–4309 (1988) (maize); Klein et al., *Bio/Technology* 6:559–563 (1988) (maize); Klein et al., *Plant Physiol.* 91:440–444 (1988) (maize); Fromm et al., *Bio/Technology* 8:833–839 (1990); and Gordon-Kamm et al., *Plant Cell* 2:603–618 (1990) (maize); Svab et al., *Proc. Natl. Acad. Sci. USA* 87:8526–8530 (1990)(tobacco chloroplasts); Gordon-Kamm et al. in "Transgenic Plants", vol. 2., pp. 21–33, pub. by Academic Press (1993)(maize).

Once a chimeric gene encoding a G10H enzyme has been transformed into a particular plant species, it may be propagated in that species or moved into other varieties of the same species, particularly including commercial varieties, using traditional breeding techniques. Alternatively, the coding sequence for a G10H enzyme may be isolated, genetically engineered for optimal expression and then transformed into the desired variety.

The present invention is further directed to transgenic plant tissue, including plants, seeds, and cultured tissue, stably transformed with at least one chimeric gene capable of expressing a G10H enzyme in the plant tissue. Expression of such a chimeric gene results in an increase in the level of the encoded G10H enzyme.

Transgenic plant tissue of the invention contains enhanced levels of terpenoid indole alkaloids resulting from the expression of the chimeric gene contained therein which encodes a G10H enzyme. Such terpenoid indole alkaloids include Iboga type alkaloids, Corynanthean type alkaloids, Strychnan type alkaloids, and Aspidospermatan type alkaloids. (see "The Alkaloids" volume 27, Chemistry and Pharmacology. ed by Brossi, Academic Press (1986; "Biosynthesis and accumulation of indole alkaloids in cell suspension cultures of Catharanthus roseus cultivars" in "Primary and Secondary Metabolism of Plant Cell Cultures", pp. 143–153, ed. by Neumann, Barz and Reinhard, Springer Veralg, Berlin Heidelberg (1985). The statement "enhanced levels of terpenoid indole alkaloids" is intended to mean levels of terpenoid indole alkaloids greater than that found in corresponding non-transgenic tissue which does not contain a chimeric gene capable of expressing a G10H enzyme in the plant tissue, but does contain the terpenoid indole alkaloid biosynthetic pathway.

In addition to participating in the biosynthesis of terpenoid indole alkaloids, G10H enzyme is also involved in the biosynthesis of iridoid insect (e.g. aphid) pheromones in plant species which naturally produce such pheromones, such as *Nepeta mussinii* (see, e.g. "Potential of Secondary Metabolites in Genetic Engineering of Crops for Resistance" by Hallahan, D. L. et al., in "Plant Genetic Manipulation for Crop Protection", ed. by Gatehouse, A. M. R. et al, pub. by CAB International, pp. 215–248 (1992). Trangenic plants and plant tissue of the invention from such species are contemplated to contain enhanced levels of iridoid insect pheromones resulting from the expression of the chimeric gene contained therein which encodes a G10H enzyme. The statement "enhanced levels of iridoid insect pheromones" is intended to mean levels of iridoid pheromones greater than that found in corresponding non-transgenic tissue which does not contain a chimeric gene capable of expressing a G10H enzyme in the plant tissue.

Representative plants of the invention include any plants which produce terpenoid indole alkaloids and/or iridoid insect pheromones by a pathway which includes the conversion of geraniol/nerol to its 10-hydroxy derivative form. Preferred are plants which currently serve as a source of terpenoid indole alkaloids such as *Catharanthus roseus, Vinca minor, Lonicera morrow* and the like (see Madyastha, K. M. et al., "Enzymology of Indole Alkaloid Biosynthesis" pp 85–129, in "Recent Advances in Phytochemistry", Vol 13 "Topics in the Biochemistry of Natural Products", ed by Swain and Wallers, pub. by Plenum Press, New York (1978)) or plants which serve as a source of iridoid insect pheromones such as *Nepeta mussinii* (see Hallahan, D. L. et al, "Potential of Secondary Metabolites in Genetic Engineering of Crops for Resistance", in "Plant Genetic Manipulation for Crop Protection", ed. by Gatehouse, A. M. R. et al, pub. by CAB International, pp. 215–248 (1992)).

Terpenoid indole alkaloids may be extracted and purified from transgenic plants of the invention which overproduce them in the same manner described for their extraction and purification from unmodified plants or tissue culture (see· U.S. Pat. No. 4,910,138 issued Mar. 20, 1990 to Kazumasa, H. et al.; U.S. Pat. No. 4,831,133 issued May 16, 1989 to Goodbody, A. E. et al.; U.S. Pat. No. 4,749,787 issued Jun. 7, 1988 to Guanasekera, S. P.; Van der Heijden, R et al., *J Chromatogr* 396: 287–295 (1987); Van der Heijden, R et al., *J Chromatogr* 396: 410–415 (1987).

Terpenoid indole alkaloids obtained from the plants of the invention may be used as pharmaceuticals in the same manner terpenoid indole alkaloids obtained from unmodified plants are used (see volume 27 of "The Alkaloids", Chemistry and Pharmacology. ed by Brossi, Academic Press (1986)).

Iridoid insect pheromones may also be extracted and purified from transgenic plants of the invention which overproduce them. Such pheromones are useful in insecticide preparations as attractants (see Hallahan, D. L. et al, *supra*.(1992)). In addition transgenic plants of the invention which produce enhanced levels of iridoid insect pheromones may themselves be used as insect attractants or "traps" as a means for deterring insect infestation of neighboring plants see Hallahan, D. L. et al., *Biochemical Society Transactions* 21:1068–1073 (1993)).

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by T. Maniatis, E. F. Fritsch and J. Sambrook, *Molecular Cloning: A Laboratory manual*, Cold Spring Harbor laboratory, Cold Spring Harbor, N.Y. (1982) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

EXAMPLE 1

Cloning of the Arabidopsis cDNA Encoding Geraniol/Nerol 10-hydroxylase (G10H)

Total RNA was prepared from 7-d-old Arabidopsis seedlings ecotype Columbia (Lehle Seeds Tucson, Ariz.) by phenol/chloroform extraction followed by lithium chloride precipitation. poly(A)+RNA was isolated from the total RNA using a poly(A)+Quick mRNA isolation kit (Stratagene, LaJolla, Calif.). A cDNA library was constructed from the poly(A)+RNA in the bacteriophage vector lambda ZAPII (Stratagene) using the Uni-ZAP XR Gigapack II Gold cloning kit (Stratagene) as described in the manufacturers' instruction.

Polymerase Chain Reaction

First-strand cDNA was synthesized from 1 µg of the poly(A)+RNA prepared as described above, and a part of this was used as a template for PCR with with a sense, 5'-AARYTICCICCIGGICC-3' (SEQ ID NO:13), primer and an antisense, 5'-GGRTCICKIWCIARGCCCAIGCRTT-3' (SEQ ID NO:4), primer designed from conserved amino acid sequences in plant P450s; KLPPGP (SEQ ID NO:5) in the N-terminal region and NAWALA(G)RDP (SEQ ID NO:6) encoded in the region about 150 bp upstream the heme-binding Cys residue, respectively. The PCR was carried out in 100 µl of a reaction mixture consisting of 10 mM of Tris-HCl (pH 8.3) containing 10 µl of the primers, 200 µM dATP, 200 µM dCTP, 200 µM dTTP, 200 µM dGTP, 2 mM MgCl₂,50 mM KCl, 25 units/mL AmpliTaq DNA polymerase (Perkin Elmer/Cetus). The reaction was performed through 35 cycles of 30 sec at 94° C., 30 sec at 50° C. and 90 sec at 72° C. using a thermal cycler (Perkin Elmer/Cetus, model 480). PCR products were separated by low-melting agarose gel (2%) electrophoresis. A major band (1.2 kb), which are thought to consist of fragments derived from different P450 genes, was isolated from the gel and cloned into the PCRII vector using a TA cloning kit (Invitorgen). The cloned PCR products were divided into several groups according to restriction patterns obtained by the digestion with EcoRI, XhoI and HindIII. The amino acid sequences were deduced from the DNA sequences determined from the inserts and compared with those of the P450s available. The DNA inserts, of which the deduced amino acid sequences showed significant homologies with known P450s, were used to isolate its corresponding full-length clone. Practically, the DNA inserts were labeled with [$^{32}$P]-dCTP by random priming labeling method and used as a probe to screen 600,000 plaques from the Arabidopsis cDNA library.

One of the obtained P450 clones, designated P450-4, was determined to encode a geraniol/nerol 10-hydroxylase. The geraniol/nerol 10-hydroxylase DNA coding sequence elucidated from this clone is provided in SEQ ID No. 1. The amino acid sequence encoded by this DNA sequence is provided in SEQ ID No. 2. This amino acid sequence has a signal sequence at its N-terminus which exhibits general properties of an endoplasmic reticulum (ER) insertion signal sequence. Microsomal cytochromes P450 are synthesized in the rough ER. The N-terminal signal sequence is involved in anchoring newly synthesized P450 protein to the cytoplasmic surface of ER membrane. The insertion of the protein into the membrane is dependent on the presence of signal recognition particle (See Sakaguchi, M. et al., *Proc Natl Acad Sci USA* 81: 3361–3363 (1984)). An essential feature of the signal sequence elements is a hydrophobic segment of sufficient length, 7–15 residues in cleaved signals, and approximately 20 residues in uncleaved signals and stop-transfer sequences. (Nelson, D. R. and Strobel, H. W. *J. Biol. Chem.* 26: 6038–6050 (1988); Beltzer, J. P. et al., *J. Biol. Chem.* 266: 973–978 (1991); Edwards, R. B. et al., *Biochemistry* 30: 71–76 (1991)).

P450-4 was expressed using the baculovirus expression vector system as described in Nagai, A. et al., *Arch. Biochem. Biophys.* 295: 235–239 (1992). *Spodoptera furugiperda* (Sf21) cells were maintained at 27° C. as a monolayer culture in Grace's medium supplemented with 0.33% TC yeastolate, 0.33% lactoalbumin, 10% fetal bovine serum. For the suspension culture of the cell as surfactant Pluoronic F-68 (BASF) was added at 0.1% in the medium. For the expression of P450-4, 200 µM 5-aminolevulinic acid and 200 µM ferrous citrate were added to the culture medium.

The full-length P450-4 cDNA was cloned into a plasmid, pVL1392 (Invitorgen) and used for transfection of Sf21 using an infectious baculovirus DNA (BaculoGold™, Pharmingen) according to the method described previously (Nagai et al., *supra*). The expressed P450-4 was purified from the infected Sf21 cells. Namely, the cells were sonicated, and an insoluble fraction was obtained by centrifugation at 100,000×g for 1 h. The pellet, which contains heavy membranes and microsomes, was homogenized with buffer A containing 20 mM potassium phosphate (pH 7.25), 20% glycerol and 1 mM dithiothreitol, and proteins were solubilized in buffer A supplemented with 1% Emulgen 913 (Kao Atlas, Osaka, Japan) (buffer B). After centrifugation at 100,000×g for 1 h, the supernatant was applied to a DEAE Sepharose column equilibrated with buffer B. P450-4 passed through the column was applied to a hydroxylapatite column equilibrated with buffer B. The column was washed thoroughly to remove Emulgen 913 from the sample with buffer A. When the absorption at 280 nm derived from the detergent disappeared from the buffer, P450-4 was eluted from the column with 0.3M potassium phosphate buffer containing 20% glycerol and 1 mM dithiothreitol.

Determination of Geraniol/Nerol 10-hydroxylase Activity

[1-$^{3}$H]geraniol and [1-$^{3}$H]nerol were synthesized (Meijer et al., *J Chromatogr,* 635: 237–239 (1993)). The G10H activity was reconstituted with the partially purified P450-4 as described previously (Mizutani et al., *Plant Cell Physiol.* 34: 481–488 (1993)). The reaction mixture consisted of 10 nM P450, 0.2 unit/mL of NADPH-P450 reductase, 0.01% sodium cholate, 1 µg/mL dilauroylphosphatidylcholine, 50 mM potassium phosphate (pH 7.25), 100 µM [1$^{3}$H]geraniol (or [1-$^{3}$H]nerol) and 1 mM NADPH. The reaction was initiated by the addition of NADPH and terminated after the incubation at 30° C. for 1 h by adding 20 µl of 0.2M HCl and 30 µM of 30% (w/v) trichloroacetic acid. After centrifugation at 10,000×g for 5 min, the supernatant was extracted twice with ethyl acetate and the organic phase was concentrated under the stream of nitrogen gas. The residue was dissolved in 50 µl of acetone and a 10 µl aliquot was subjected to TLC analysis. The plate was developed with toluene-ethyl acetate-acetone (6:4:1, v/v/v). The substrate and product were visualized on the plate by spraying with anisaldehyde-acetic acid-methanol-sulfuric acid (1:20:170:10, v/v/v/v). The radioactivity from the reaction product was estimated with an radio-image analyzer (BAS2000, Fuji Film, Tokyo). The product purified by TLC was analyzed by NMR, and it was confirmed that 10-hydroxylated geraniol (or nerol) was formed via the reaction catalyzed by P450-4.

EXAMPLE 2

Isolation of Additional G10H Genes Based on Sequence Homology to the Arabidopsis G10H Coding Sequences A phage or plasmid cDNA library is plated at a density of approximately 10,000 plaques on a 10 cm Petri dish, and filter lifts of the plaques are made after overnight growth of the plates at 37° C. The plaque lifts are probed with the cDNA set forth in SEQ ID NO:1, labeled with $^{32}$P-dCTP by the random priming method by means of a PrimeTime kit (International Biotechnologies, Inc., New Haven, Conn.). Hybridization conditions are 7% sodium dodecyl sulfate (SDS), 0.5M NaPO$_4$ pH 7.0, 1 mM EDTA at 50° C. After hybridization overnight, the filters are washed with 2× SSC, 1% SDS. Positively hybridizing plaques are detected by autoradiography. After purification to single plaques, cDNA inserts are isolated, and their sequences determined by the chain termination method using dideoxy terminators labeled with fluorescent dyes (Applied Biosystems, Inc., Foster City, Calif.).

The standard experimental protocol described above can be used by one of skill in the art to obtain G10H genes sequentially homologous to the known G10H coding sequences from any other eukaryote, particularly other higher plant species. This protocol is particularly useful for obtaining G10H genes which share 50% or greater homology to the G10H coding sequence used as a probe.

Applicability of this protocol for obtaining G10H genes from other plants has been supported by the observation of specific hybridization of an Arabidopsis G10H coding sequence probe to discrete DNA restriction fragments from the Zea mays genome in a standard Southern blot. This result indicates that the degree of homology between the Arabidopsis and Zea mays G10H coding sequences is sufficient for the Arabidopsis sequence to specifically hybridize to the Zea mays sequence present among a pool of DNA representing the entire maize genome. In view of this Southern result, specific hybridization of the Arabidopsis G10H coding sequence to a maize cDNA library according to the protocol above would be expected since such a library represents only a subset of the entire maize genomic DNA (i.e. the coding portion).

EXAMPLE 3

Construction of Plant Transformation Vectors

Numerous transformation vectors are available for plant transformation, and genes encoding G10H enzymes can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptII gene which confers resistance to kanamycin and related antibiotics (Messing & Vierra, Gene 19: 259–268 (1982); Bevan et al., Nature 304:184–187 (1983)), the bar gene which confers resistance to the herbicide phosphinothricin (White et al., Nucl Acids Res 18: 1062 (1990), Spencer et al. Theor Appl Genet 79: 625–631(1990)), the hph gene which confers resistance to the antibiotic hygromycin (Blochinger & Diggelmann, Mol Cell Biol 4: 2929–2931), and the dhfr gene, which confers resistance to methotrexate (Bourouis et al., EMBO J. 2(7): 1099–1104 (1983)).

(1) Construction of Vectors Suitable for Agrobacterium Transformation

Many vectors are available for transformation using Agrobacterium tumefaciens. These typically carry at least one T-DNA border sequence and include vectors such as pBIN19 (Bevan, Nucl. Acids Res. (1984)) and pXYZ. Below the construction of two typical vectors is described.

Construction of pCIB200 and pCIB2001

The binary vectors pCIB200 and pCIB2001 are used for the construction of recombinant vectors for use with Agrobacterium and was constructed in the following manner. pTJS75kan was created by NarI digestion of pTJS75 (Schmidhauser & Helinski, J Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982); Bevan et al., Nature 304: 184–187 (1983); McBride et al., Plant Molecular Biology 14: 266–276 (1990) ). XhoI linkers were ligated to the EcoRV fragment of pCIB7 which contains the left and right T-DNA borders, a plant selectable nos/nptII chimeric gene and the pUC polylinker (Rothstein et al., Gene 53: 153–161 (1987)), and the XhoI-digested fragment was cloned into SalI-digested pTJS75kan to create pCIB200 (see also example 19 of EP 0 332 104). pCIB200 contains the following unique polylinker restriction sites: EcoRI, SstI, KpnI, BglII, XbaI, and SalI pCJB2001 is a derivative of pCIB200 which created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between E. coli and other hosts, and the OriT and OriV functions also from RK2. The pCIB2001 polylinker is suitable for the cloning of plant expression cassettes containing their own regulatory signals.

Construction of pCIB10 and Hygromycin Selection Derivatives thereof

The binary vector pCIB10 contains a gene encoding kanamycin resistance for selection in plants, T-DNA right and left border sequences and incorporates sequences from the wide host-range plasmid pRK252 allowing it to replicate in both E. coli and Agrobacterium. Its construction is described by Rothstein et al., Gene 53: 153–161 (1987). Various derivatives of pCIB10 have been constructed which incorporate the gene for hygromycin B phosphotransferase described by Gritz et al., Gene 25: 179–188 (1983)). These derivatives enable selection of transgenic plant cells on hygromycin only (pCIB743), or hygromycin and kanamycin (pCIB715, pCIB717).

(2) Construction of Vectors Suitable for non-Agrobacterium Transformation.

Transformation without the use of Agrobacterium tumefaciens circumvents the requirement for T-DNA sequences in the chosen transformation vector and consequently vectors lacking these sequences can be utilized in addition to vectors such as the ones described above which contain T-DNA sequences. Transformation techniques which do not rely on Agrobacterium include transformation via particle bombardment, protoplast uptake (e.g. PEG and electroporation) and microinjection. The choice of vector depends largely on the preferred selection for the species being transformed. Below, the construction of some typical vectors is described.

Construction of pCIB3064 pCIB3064 is a pUC-derived vector suitable for direct gene transfer techniques in combination with selection by the herbicide basta (or phosphinothricin). The plasmid pCIB246 comprises the CaMV 35S promoter in operational fusion to the E. coli GUS gene and the CaMV 35S transcriptional terminator and is described in the PCT published application WO 93/07278. The 35S promoter of this vector contains two ATG sequences 5' of the start site. These sites were mutated using standard PCR techniques in such a way as to remove the ATGs and generate the restriction sites SspI and PvuII. The new restriction sites were 96 and 37 bp away from the unique SalI site and 101 and 42 bp away from the actual start site. The resultant derivative of pCIB246 was designated pCIB3025. The GUS gene was then excised from pCIB3025 by digestion with SalI and SacI, the termini rendered blunt and religated to generate plasmid pCIB3060. The plasmid pJIT82 was obtained from the John Innes Centre, Norwich and the a 400 bp SmaI fragment containing the bar gene from *Streptomyces viridochromogenes* was excised and inserted into the HpaI site of pCIB3060 (Thompson et al. EMBO J 6: 2519–2523 (1987)). This generated pCIB3064 which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

Construction of pSOG19 and pSOG35 pSOG35 is a transformation vector which utilizes the *E. coli* gene dihydrofolate reductase (DHFR) as a selectable marker conferring resistance to methotrexate. PCR was used to amplify the 35S promoter (~800 bp), intron 6 from the maize Adh1 gene (~550 bp) and 18 bp of the GUS untranslated leader sequence from pSOG10. A 250 bp fragment encoding the *E. coli* dihydrofolate reductase type II gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generated the vector pSOG35. pSOG19 and pSOG35 carry the pUC gene for ampicillin resistance and have HindIII, SphI, PstI and EcoRI sites available for the cloning of foreign sequences.

EXAMPLE 4

Construction of Plant Expression Cassettes

Gene sequences intended for expression in transgenic plants are firstly assembled in expression cassettes behind a suitable promoter and upstream of a suitable transcription terminator. These expression cassettes can then be easily transferred to the plant transformation vectors described above in Example 3.

Promoter Selection

The selection of a promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and this selection will reflect the desired location of expression of the transgene. Alternatively, the selected promoter may drive expression of the gene under a light-induced or other temporally regulated promoter. A further alternative is that the selected promoter be chemically regulated. This would provide the possibility of inducing expression of the transgene only when desired and caused by treatment with a chemical inducer.

Transcriptional Terminators

A variety of transcriptional terminators are available for use in expression cassettes. These are responsible for the termination of transcription beyond the transgene and its correct polyadenylation. Appropriate transcriptional termi-nators and those which are known to function in plants and include the CaMV 35S terminator, the tml terminator, the nopaline synthase terminator, the pea rbcS E9 terminator. These can be used in both monocotyledons and dicotyledons.

Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop.* 1: 1183–1200 (1987)). In the same experimental system, the intron from the maize bronze1 gene had a similar effect in enhancing expression (Callis et al., *supra*). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693–8711 (1987); Skuzeski et al. *Plant Molec. Biol.* 15: 65–79 (1990))

Targeting of the Gene Product Within the Cell

Various mechanisms for targeting gene products are known to exist in plants and the sequences controlling the functioning of these mechanisms have been characterized in some detail. These mechanisms generally utilize identified transit peptides or internal amino acid sequences which have been found to target associated proteins to various cellular compartments such as the chloroplast, the mitochondrion, the peroxisome, the nucleus, the ER, the apoplast, and the vacuole.

Chloroplast Targeting

The targeting of gene products to the chloroplast is controlled by a signal sequence found at the amino terminal end of various proteins and which is cleaved during chloroplast import yielding the mature protein (e.g. Comai et al., *J. Biol. Chem.* 263: 15104–15109 (1988)). These signal sequences can be fused to heterologous gene products to effect the import of heterologous products into the chloroplast (van den Broeck et al. *Nature* 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized.

Chen & Jagendorf (*J. Biol. Chem.* 268: 2363–2367 (1993)) have described the successful use of a chloroplast transit peptide for import of a heterologous transgene. This peptide used is the transit peptide from the rbcS gene from *Nicotiana plumbaginifolia* (Poulsen et al. *Mol. Gen. Genet.* 205: 193–200 (1986)). Using the restriction enzymes DraI and SphI, or Tsp509I and SphI the DNA sequence encoding this transit peptide can be excised from plasmid prbcS-8B (Poulsen et al. *supra*) and manipulated for use with any of the constructions described above. The DraI-SphI fragment extends from −58 relative to the initiating rbcS ATG to, and including, the first amino acid (also a methionine) of the mature peptide immediately after the import cleavage site, whereas the Tsp509I-SphI fragment extends from −8 relative to the initiating rbcS ATG to, and including, the first amino acid of the mature peptide. Thus, these fragment can be appropriately inserted into the polylinker of any chosen expression cassette generating a transcriptional fusion to the untranslated leader of the chosen promoter (e.g. 35S, PR-1a, actin, ubiquitin etc.), whilst enabling the insertion of a BBE gene in correct fusion downstream of the transit peptide. Constructions of this kind are routine in the art. For example, whereas the DraI end is already blunt, the 5' Tsp509I site may be rendered blunt by T4 polymerase treatment, or may alternatively be ligated to a linker or adaptor sequence to facilitate its fusion to the chosen promoter. The 3' SphI site may be maintained as such, or may alternatively be ligated to adaptor of linker sequences to facilitate its insertion into the chosen vector in such a way as to make available appropriate restriction sites for the subsequent insertion of a selected APS gene. Ideally the ATG of the SphI site is maintained and comprises the first ATG of the selected APS gene. Chen & Jagendorf (*supra*) provide consensus sequences for ideal cleavage for chloroplast import, and in each case a methionine is preferred at the first position of the mature protein. At subsequent positions there is more variation and the amino acid may not be so critical. In any case, fusion constructions can be assessed for efficiency of import in vitro using the methods described by Bartlett et al. (In: Edelmann et al. (Eds.) Methods in Chloroplast Molecular Biology, Elsevier. pp 1081–1091 (1982)) and Wasmann et al. (*Mol. Gen. Genet.* 205: 446–453 (1986)). Typically the best approach may be to generate fusions using the selected BBE gene with no modifications at the aminoterminus, and only to incorporate modifications when it is apparent that such fusions are not chloroplast imported at high efficiency, in which case modifications may be made in accordance with the established literature (Chen & Jagendorf, *supra*; Wasman et al., *supra*; Ko & Ko, *J. Biol. Chem.* 267: 13910–13916 (1992)).

Targeting to Other Plant Cellular Compartments

Other gene products are localized to organelles such as the mitochondrion and the peroxisome (e.g. Unger et al. *Plant Molec. Biol.* 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting to cellular protein bodies has been described by Rogers et al., *Proc. Natl. Acad. Sci. USA* 82: 6512–6516 (1985)).

In addition sequences have been characterized which cause the targeting of gene products to other cell compartments. Amino terminal sequences are responsible for targeting to the ER, the apoplast, and extracellular secretion from aleurone cells (Koehler & Ho, *Plant Cell* 2: 769–783 (1990)). Additionally, amino terminal sequences in conjunction with carboxy terminal sequences are responsible for vacuolar targeting of gene products (Shinshi et al., *Plant Molec. Biol.* 14: 357–368 (1990)).

Transgene Targeting

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the transgene ATG or alternatively replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) *Methods in Chloroplast Molecular Biology*, Elsevier. pp 1081–1091 (1982); Wasmann et al. *Mol. Gen. Genet.* 205: 446–453 (1986)). These construction techniques are well known in the art and are equally applicable to mitochondria and peroxisomes. The choice of targeting which may be required for expression of the transgenes will depend on the cellular localization of the precursor required as the starting point for a given pathway. This will usually be cytosolic or chloroplastic, although it may is some cases be mitochondrial or peroxisomal. The products of transgene expression will not normally require targeting to the ER, the apoplast or the vacuole.

The above described mechanisms for cellular targeting can be utilized not only in conjunction with their cognate promoters, but also in conjunction with heterologous promoters so as to effect a specific cell targeting goal under the transcriptional regulation of a promoter which has an expression pattern different to that of the promoter from which the targeting signal derives.

EXAMPLE 6

Transformation of Dicotyledons

Transformation techniques for dicotyledons are well known in the art and include Agrobacterium-based techniques and techniques which do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., *EMBO J* 3: 2717–2722 (1984), Potrykus et al., *Mol. Gen. Genet.* 199: 169–177 (1985), Reich et al., *Biotechnology* 4: 1001–1004 (1986), and Klein et al., *Nature* 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. The many crop species which are routinely transformable by Agrobacterium include tobacco, tomato, sunflower, cotton, oilseed rape, potato, soybean, alfalfa and poplar (EP 0 317 511 (cotton), EP 0 249 432 (tomato, to Calgene), WO 87/07299 (Brassica, to Calgene), U.S. Pat. No. 4,795,855 (poplar)). Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agrobacterium strain either on a co-resident Ti plasmid or chromosomally (e.g. strain CIB542 for pCIB200 and pCIB2001 (Uknes et al. *Plant Cell* 5: 159–169 (1993)). The transfer of the recombinant binary vector to Agrobacterium is accomplished by a triparental mating procedure using *E.* coli carrying the recombinant binary vector, a helper *E. coli* strain which carries a plasmid such as pRK2013 and which is able to mobilize the recombinant binary vector to the target Agrobacterium strain. Alternatively, the recombinant binary vector can be transferred to Agrobacterium by DNA transformation (Höfgen & Willmitzer, *Nucl. Acids Res.* 16: 9877(1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

EXAMPLE 7

Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. *Biotechnology* 4: 1093–1096 (1986)).

Patent Applications EP 0 292 435 (to Ciba-Geigy), EP 0 392 225 (to Ciba-Geigy) and WO 93/07278 (to Ciba-Geigy) describe techniques for the preparation of callus and protoplasts from an elite inbred line of maize, transformation of protoplasts using PEG or electroporation, and the regeneration of maize plants from transformed protoplasts. Gordon-Kamm et al., *Plant Cell* 2: 603–618 (1990)) and Fromm et al., *Biotechnology* 8: 833–839 (1990)) have published techniques for transformation of A188-derived maize line using particle bombardment. Furthermore, application WO 93/07278 (to Ciba-Geigy) and Koziel et al., *Biotechnology* 11: 194–200 (1993)) describe techniques for the transformation of élite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al., *Plant Cell Rep* 7: 379–384 (1988); Shimamoto et al. *Nature* 338: 274–277 (1989); Datta et al. *Biotechnology* 8: 736–740 (1990)). Both types are also routinely transformable using particle bombardment (Christou et al. *Biotechnology* 9: 957–962 (1991)).

Patent Application EP 0 332 581 (to Ciba-Geigy) describes techniques for the generation, transformation and regeneration of Pooideae protoplasts. These techniques allow the transformation of Dactylis and wheat. Furthermore, wheat transformation was been described by Vasil et al., *Biotechnology* 10: 667–674 (1992)) using particle bombardment into cells of type C long-term regenerable callus, and also by Vasil et al., *Biotechnology* 11: 1553–1558 (1993)) and Weeks et al., *Plant Physiol.* 102: 1077–1084 (1993) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashige & Skoog, *Physiologia Plantarum* 15: 473–497 (1962)) and 3 mg/l 2,4-D for induction of somatic embryos which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics' helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contained half-strength MS, 2% sucrose, and the same concentration of selection agent. Patent application Ser. No. 08/147,161 describes methods for wheat transformation and is hereby incorporated by reference.

Although only a limited number of exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the claims.

We claim:

1. An isolated DNA molecule encoding a protein from a plant having geraniol/nerol 10-hydroxylase (G10H) activity, wherein said DNA molecule hybridizes to the nucleotide sequence set forth in SEQ ID NO:1 under the following conditions: hybridization in 7% sodium dodecyl sulfate (SDS), 0.5M NaPO$_4$ pH 7.0, 1 mM EDTA at 50° C.; and wash with 2× SSC, 1% SDS.

2. The isolated DNA molecule of claim 1, wherein said plant is an Arabidopsis species.

3. A chimeric gene capable of expressing a G10H enzyme comprising a promoter operably linked to the DNA molecule of claim 1.

4. A vector comprising the chimeric gene of claim 3, wherein said vector is capable of being stably transformed into a host cell.

5. An isolated host cell stably transformed with the vector of claim 4, wherein said host cell is capable of expressing said DNA molecule.

6. An isolated host cell of claim 5 selected from the group consisting of a plant cell, a bacterial cell, a yeast cell, and an insect cell.

7. An isolated host cell of claim 6, which is a plant cell.

8. The isolated DNA molecule of claim 1, wherein said DNA molecule comprises the coding sequence set forth in SEQ ID NO:1.

9. An isolated DNA molecule encoding a protein from a plant having geraniol/nerol 10-hydroxylase (G10H) activity, wherein said DNA molecule encodes a protein comprising the amino acid sequence set forth in SEQ ID NO:2.

10. The isolated DNA molecule of claim 9, wherein said plant is an Arabidopsis species.

11. The isolated DNA molecule of claim 9, wherein said DNA molecule comprises the coding sequence set forth in SEQ ID NO:1.

12. A chimeric gene capable of expressing a G10H enzyme comprising a promoter operably linked to the DNA molecule of claim 9.

13. A vector comprising the chimeric gene of claim 12, wherein said vector is capable of being stably transformed into a host cell.

14. An isolated host cell stably transformed with the vector of claim 13, wherein said host cell is capable of expressing said DNA molecule.

15. An isolated host cell of claim 14 selected from the group consisting of a plant cell, a bacterial cell, a yeast cell, and an insect cell.

16. An isolated host cell of claim 15, which is a plant cell.

17. An isolated DNA molecule encoding a protein from a plant having geraniol/nerol 10-hydroxylase (G10H) activity, wherein said DNA molecule hybridizes to the isolated DNA molecule of claim 9 under the following conditions: hybridization in 7% sodium dodecyl sulfate (SDS), 0.5M NaPO$_4$ pH 7.0, 1 mM EDTA at 50° C.; and wash with 2× SSC, 1% SDS.

* * * * *